United States Patent [19]

Thiem et al.

[11] 4,341,902

[45] Jul. 27, 1982

[54] PROCESS FOR THE PRODUCTION OF 5-NITRO-ACET-2,4-XYLIDINE

[75] Inventors: Karl W. Thiem, Charleston; Daniel P. Vanderpool, Hanahan, both of S.C.

[73] Assignee: Mobay Chemical Corporation, Pittsburgh, Pa.

[21] Appl. No.: 278,545

[22] Filed: Jun. 26, 1981

[51] Int. Cl.³ .......................................... C07C 102/00
[52] U.S. Cl. .................................................. 564/218
[58] Field of Search ........................................ 564/218

[56] References Cited

U.S. PATENT DOCUMENTS

| | | | |
|---|---|---|---|
| 3,480,681 | 11/1969 | Zanella | 260/646 |
| 3,506,725 | 4/1970 | Sturm et al. | 260/645 |
| 3,816,551 | 6/1974 | Lee | 260/646 |
| 3,894,078 | 7/1975 | Fridinger | 260/501.19 |
| 4,013,444 | 3/1977 | Fridinger | 71/76 |
| 4,139,558 | 2/1979 | Stopp et al. | 260/562 A |
| 4,151,203 | 4/1979 | Cheng | 564/218 |
| 4,235,789 | 11/1980 | Stout | 260/380 |
| 4,246,180 | 1/1981 | Leisier et al. | 260/371 |

*Primary Examiner*—Arthur P. Demers
*Attorney, Agent, or Firm*—Gene Harsh; Joseph C. Gil

[57] ABSTRACT

The present invention is directed to a process for preparing 5-nitro-acet-2,4-xylidine comprising
(a) dissolving acet-2,4-xylidine in an aqueous sulfuric acid solution,
(b) nitrating the resultant solution with a mixture of nitric acid and sulfuric acid,
(c) adding the resultant nitration mixture to an aqueous sulfuric acid solution containing from 25 to 45% by weight of sulfuric acid, while maintaining the temperature at from 20° to 50° C. to thereby produce a slurry containing sulfuric acid in a concentration of from 30 to 50% by weight based solely on the weight of water and sulfuric acid, the total amount of sulfuric acid in said slurry being such that the molar ratio of sulfuric acid to the nitro-acet-2,4-xylidine isomers is from 53:1 to 10:1, and
(d) recovering 5-nitro-acet-2,4-xylidine.

7 Claims, No Drawings

PROCESS FOR THE PRODUCTION OF 5-NITRO-ACET-2,4-XYLIDINE

BACKGROUND OF THE INVENTION

The present invention relates to an improved process for the production of 5-nitro-acet-2,4-xylidine.

The compound, 5-amino-acet-2,4-xylidine, is known in the art and is used as an intermediate for the preparation of 5-acetamido-2,4-dimethyl-trifluoromethanesulfonanilide (see, e.g., U.S. Pat. Nos. 3,894,078 and 4,013,444). In general, 5-amino-acet-2,4-xylidine can be produced by catalytically hydrogenating 5-nitro-acet-2,4-xylidine, with the 5-nitro-acet-2,4-xylidine being produced by the nitration of acet-2,4-xylidine. Following nitration, the nitrated mixture is generally added to water. Unfortunately, the 5-nitro-acet-2,4-xylidine is not precipitated in pure form during addition to water, but is in admixture with a substantial amount of the 3-nitro and 6-nitro isomers.

Since the ultimate purpose is to produce a relatively pure 5-amino-acet-2,4-xylidine, the art has taken two separate courses. In the first, the 5-nitro isomer is separated utilizing a relatively complex dissolving and crystallization process using organic solvents. This necessarily creates material and solvent losses. In the currently preferred mode, the nitration mixture is added to water, and the resultant isomer mixture is then hydrogenated. The desired 5-amino-compound is then separated from the hydrogenated mixture, utilizing a relatively complex separation technique.

Various processes are known for the separation of isomers in general. Thus, for example, U.S. Pat. No. 4,246,180 describes a process for separating 1-amino-4-bromoanthraquinone-2-sulfonic acid from the reaction mixture formed by brominating 1-aminoanthraquinone-2-sulfonic acid in sulfuric acid. The process consists of adjusting the sulfuric acid concentration by the addition of the reaction mixture to water or to an aqueous sulfuric acid solution. The adjusted sulfuric acid concentration is described as being from 60 to 85% by weight. Similarly, U.S. Pat. No. 4,235,789 describes a process for separating 1-amino-2-bromo-4-hydroxyanthraquinone from a reaction mixture by adjusting the sulfuric acid content in the mixture to 50 to 80% by weight. Finally, U.S. Pat. No. 3,480,681 describes a process for separating 1,2-dichloro-4-nitrobenzene from an isomeric nitration mixture of the 4-nitro and 3-nitro isomer by adding water to the nitration mixture to dilute the sulfuric acid concentration to 65 to 90% by weight. The desired isomer then selectively, fractionally crystallizes from the nitration mixture. The use of water in separating isomers from nitration mixture is also described in U.S. Pat. Nos. 4,139,558; 3,506,725 and 3,816,551.

One object of the present invention is to provide a simple method for the separation of 5-nitro-acet-2,4-xylidine from a nitration mixture containing, in addition to the 5-nitro isomer, the 3-nitro and 6-nitro isomers. The resultant separated product can then be hydrogenated to produce 5-amino-acet-2,4-xylidine.

DESCRIPTION OF THE INVENTION

The present invention is thus directed to a process for preparing 5-nitro-acet-2,4-xylidine comprising
(a) dissolving acet-2,4-xylidine in an aqueous sulfuric acid solution,
(b) nitrating the resultant solution with a mixture of nitric acid and sulfuric acid,
(c) adding the resultant nitration mixture to an aqueous sulfuric acid solution containing from 25 to 45% by weight of sulfuric acid, while maintaining the temperature at from 20° to 50° C. to thereby produce a slurry containing sulfuric acid in a concentration of from 30 to 50% by weight, based solely on the weight of water and sulfuric acid, the total amount of sulfuric acid in said slurry being such that the molar ratio of sulfuric acid to the nitro-acet-2,4-xylidine isomers present (i.e., the 5-nitro, the 6-nitro and the 3-nitro isomers) is from 53:1 to 10:1, and
(d) recovering 5-nitro-acet-2,4-xylidine.

In the first step of the process of the present invention, acet-2,4-xylidine is first dissolved in an aqueous sulfuric acid solution. In general, the first step is conducted at a temperature of from 0° to 20° C., and preferably at a temperature of from 5°–15° C. The aqueous sulfuric acid solution used in the first step of the process generally contains from 85 to 98%, preferably 85 to 93.5%, more preferably 88 to 93% and most preferably about 90% by weight of sulfuric acid.

The resultant solution is then nitrated in a known manner, generally at a temperature of from 0° to 30° C., preferably from 0° to 10° C., and most preferably from 5° to 10° C., using a mixture of nitric acid and sulfuric acid, and preferably water (hereinafter referred to as "mixed acid"). The mixed acid used can contain from 0 to 25%, preferably from 15 to 20%, and most preferably about 20% by weight of water. The mixed acid is added in such an amount that the molar ratio of nitric acid to acet-2,4-xylidine is from 0.9:1 to 1.05:1, preferably from 0.95:1 to 1.01:1 and most preferably about 0.99:1.

Following nitration, the resultant mixture is introduced into an aqueous sulfuric acid solution containing from 25 to 45%, and preferably from 30 to 40%, by weight of sulfuric acid. The temperature is then maintained at from 20° to 50° C., and preferably at from 30° to 40° C. In a particularly preferred embodiment, the reaction mixture is introduced into a 34% sulfuric acid solution and maintained at a temperature of 30° to 40° C. by introducing ice into the mixture and by controlling the cooling. Addition of seeding crystals of 5-nitro-acet-2,4-xylidine to the dilute sulfuric acid can assist the crystallization of the desired 5-nitro isomer. After all the reaction mixture has been introduced, the resultant slurry will have a sulfuric acid concentration (based only on water and sulfuric acid) of from 30 to 50%, preferably from 40 to 48%, and most preferably from about 43 to 45% by weight. The temperature may be maintained by the addition of ice or by using cooling coils. The reaction product which precipitates out of the solution can then be filtered off at 25° to 45° C., preferably at 35° to 40° C., preferably using a filter press.

It has also been found that the total amount of sulfuric acid in the slurry should be controlled relative to the amount of nitro isomers in order to achieve both the high parity and the good yields. When the sulfuric acid concentration in the slurry is from 30 to 50% by weight, the molar ratio of sulfuric acid to nitro isomers should be from 53:1 to 10:1. The relationship between the sulfuric acid concentration in the slurry to the molar ratio of sulfuric acid to nitro isomers is said that when the sulfuric acid concentration is 30%, the molar ratio should be 53:1. Similarly if the sulfuric acid concentration is 50%, the molar ratio should be 10:1. When the sulfuric acid concentration is from 40 to 48% by weight, the molar ratio should be from 39:1 to 12:1. Finally, in the most preferred embodiment, when the sulfuric acid concentration is from 43 to 45% by weight, the molar ratio should be from 24:1 to 15:1. The amount of nitro-isomers in the slurry can be readily determined since the acet-2,-4-xylidine will react with the nitric acid present during nitration substantially stoichiometrically (i.e., generally to a degree of about 99%).

It should be emphasized that, in order to obtain the excellent results herein, the nitration mixture must be added to the aqueous sulfuric acid solution. If, for example, water is added to the reaction mixture to lower the sulfuric acid concentration, the results described herein will not be obtained. Similarly, if the reaction mixture is first added to water, and then sulfuric acid is added to increase the sulfuric acid concentration, the results described herein will not be obtained.

The invention is further illustrated but is not intended to be limited by the following Examples, in which all parts and percentages are by weight unless otherwise specified.

EXAMPLE 1

3286 parts of acet-2,4-xylidine are dissolved in 17,285 parts of aqueous sulfuric acid (about 90% by weight) and are then nitrated with 3806 parts of a mixed acid consisting of 33% by weight nitric acid, 48% by weight sulfuric acid and 19% by weight water, at a temperature maintained at from 5° to 10° C. for a period of about six to twelve hours. The reaction mixture was then introduced into an open vessel containing 44,600 parts of an aqueous sulfuric acid solution containing 30% by weight sulfuric acid. The temperature was maintained between 30° and 40° C. by addition of 7500 parts of ice and kept at that temperature for one hour. The precipitate was then filtered off on a filter press, and was washed with water until the wash water had a pH of 4.0 to 5.0.

6142 parts of reaction product containing 51% of 5-nitro-acet-2,4-xylidine were obtained. This corresponded to a yield of 2976 parts of dry 5-nitro-acet-2,4-xylidine, which corresponded to 71% of theory. The dry product was 95% pure 5-nitro isomer.

EXAMPLE 2 (comparison)

500 parts of acet-2,4-xylidine on a 100% basis were dissolved in 2430 parts of sulfuric acid, 89.8%, at 10°–15° C. and are then nitrated at 3°–8° C. with 576 parts of mixed acid consisting of 33% by weight nitric acid, 48% by weight sulfuric acid and 19% by weight water over a period of about 1.5 hours.

The reaction mixture was then introduced into another vessel containing 4600 parts of water at 30°–40° C. over a period of 1.5 hours while 406 parts ice were added to keep the temperature below 40° C.

After adding 43 parts 98% sulfuric acid, the drowning mixture was cooled to 23° C. by addition of 1540 parts of ice.

The precipitate was then filtered on a nutsch. The mother liquor contained sulfuric acid in a concentration of 28% $H_2SO_4$.

1290 parts of wet product containing 38% of 5-nitro-acet-2,4-xylidine were obtained. This corresponded to a yield of 490 parts of dry 5-nitro-acet-2,4-xylidine, which corresponded to 77% of theory. The dry product contained 86% of 5-nitro-acet-2,4-xylidine, 8.2% of 3-nitro-acet-2,4-xylidine and 3.4% of 5-nitro-acet-2,4-xylidine.

EXAMPLE 3 (comparison)

500 parts of acet-2,4-xylidine on a 100% basis were dissolved in 2430 parts of sulfuric acid, 89.8%, at 10°–15° C. and are then nitrated at 3°–8° C. with 576 parts of mixed acid consisting of 33% by weight nitric acid, 48% by weight sulfuric acid and 19% by weight water over a period of about 1.5 hours.

The reaction mixture was then introduced into another vessel containing 3572 parts of water at 30°–40° C. over a period of one hour and was externally cooled with ice/water to keep the temperature below 40° C.

After adding 38.8 parts 98% sulfuric acid, for rinsing, the drowning mixture was cooled to 23° C. by external cooling using ice/water.

The precipitate was then filtered on a nutsch. The mother liquor contained sulfuric acid in a concentration of 40% $H_2SO_4$.

1309 parts of wet product containing 39.4% of 5-nitro-acet-2,4-xylidine were obtained. This corresponded to a yield of 516 parts of dry 5-nitro-acet-2,4-xylidine, which corresponded to 81% of theory. The dry product contained 86% of 5-nitro-acet-2,4-xylidine, 10.7% of 3-nitro-acet-2,4-xylidine and 3.7% of 6-nitro-acet-2,4-xylidine.

EXAMPLES 4 THROUGH 18

In a manner similar to Example 1, about 3286 parts of acet-2,4-xylidine was dissolved in an aqueous sulfuric acid (concentration of about 90% by weight) in the amount noted in TABLE I. The mixtures were then nitrated with mixed acid (33% by weight nitric acid, 48% by weight sulfuric acid and 19% by weight water) at a temperature of from 3° to 8° C. until titration tests showed a percent nitration of from 96 to 100%. The reaction mixtures were then introduced into an open vessel containing an aqueous sulfuric acid solution, with the temperature being maintained at from 29° to 43° C. for a period of from 30 minutes to one hour. The resultant precipitates were then filtered off and washed with water until the wash water had a pH of about 4 to about 5. The resultant products were then analyzed. The various amounts of materials, concentrations and results were as indicated in Table I.

TABLE I

| Example | Amount $H_2SO_4$ Solution ,pbw | Amount Mixed Acid ,pbw | Concentration $H_2SO_4$ in Drowning Vessel before addition of reaction product | Amount $H_2SO_4$ Solution in Drowning Vessel ,pbw | Parts Reaction Product | Parts dry 5-nitro | % Theory | % dry 5-nitro isomer |
|---|---|---|---|---|---|---|---|---|
| 4 | 17,285 | 4000 | 32% | 44,000 | 7060 | 2996 | 71.5 | 95 |
| 5 | 17,485 | 3935 | 31% | 45,000 | 8303 | 3047 | 72.7 | 91 |
| 6 | 17,435 | 3995 | 33% | 42,000 | 5263 | 2934 | 70.0 | 98 |
| 7 | 17,285 | 3895 | 32% | 44,000 | 7233 | 2940 | 70.1 | 92 |
| 8 | 17,477 | 3985 | 32% | 44,000 | 6436 | 2908 | 69.4 | 96 |
| 9 | 17,365 | 3895 | 33% | 42,000 | 6987 | 2897 | 68.9 | 97 |
| 10 | 17,465 | 3870 | 31% | 45,000 | 6888 | 2803 | 66.9 | 95 |

TABLE I-continued

| Example | Amount H$_2$SO$_4$ Solution, pbw | Amount Mixed Acid, pbw | Concentration H$_2$SO$_4$ in Drowning Vessel before addition of reaction product | Amount H$_2$SO$_4$ Solution in Drowning Vessel, pbw | Parts Reaction Product | Parts dry 5-nitro | % Theory | % dry 5-nitro isomer |
|---|---|---|---|---|---|---|---|---|
| 11 | 17,445 | 3870 | 30% | 46,000 | 9421 | 3251 | 78.7 | 91 |
| 12 | 17,415 | 3950 | 31% | 45,000 | 7172 | 2999 | 71.5 | 95 |
| 13 | 17,415 | 3920 | 32% | 44,000 | 7477 | 3077 | 73.4 | 95 |
| 14 | 17,415 | 3870 | 33% | 42,000 | 8476 | 2660 | 63.4 | 95 |
| 15 | 17,415 | 3870 | 32% | 44,000 | 6188 | 2481 | 59.2 | 97 |
| 16 | 17,415 | 4110 | 33% | 42,000 | 6968 | 3265 | 77.9 | 97 |
| 17 | 17,415 | 3870 | 37% | 38,000 | 4671 | 2808 | 67.0 | 99 |
| 18 | 17,415 | 4020 | 32% | 44,000 | 7229 | 2754 | 65.7 | 90 |

What is claimed is:

1. A process for preparing 5-nitro-acet-2,4-xylidine comprising
   (a) dissolving acet-2,4-xylidine in an aqueous sulfuric acid solution,
   (b) nitrating the resultant solution with a mixture of nitric acid and sulfuric acid,
   (c) adding the resultant nitration mixture to an aqueous sulfuric acid solution containing from 25 to 45% by weight of sulfuric acid, while maintaining the temperature at from 20° to 50° C. to thereby produce a slurry containing sulfuric acid in a concentration of from 30 to 50% by weight based solely on the weight of water and sulfuric acid, the total amount of sulfuric acid in said slurry being such that the molar ratio of sulfuric acid to the nitro-acet-2,4-xylidine isomers is from 53:1 to 10:1, and
   (d) recovering 5-nitro-acet-2,4-xylidine.

2. The process of claim 1 wherein in step (c) the nitration mixture is added to an aqueous sulfuric acid solution containing 30 to 40% by weight of sulfuric acid.

3. The process of claim 2, wherein in step (c) said temperature is maintained at from 30° to 40° C.

4. The process of claim 2 wherein said slurry contains 40 to 48% sulfuric acid.

5. The process of claim 4, wherein said molar ratio is from 39:1 to 12:1.

6. The process of claim 4 wherein said slurry contains from 43 to 45% sulfuric acid.

7. The process of claim 6 wherein said molar ratio is from 24:1 to 15:1.

* * * * *